US00PP30195P2

(12) United States Plant Patent
Koot

(10) Patent No.: US PP30,195 P2
(45) Date of Patent: Feb. 12, 2019

(54) ***PETUNIA* PLANT NAMED 'DOPETSMIMAR'**

(50) Latin Name: *Petunia X hybrida*
Varietal Denomination: Dopetsmimar

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,759

(22) Filed: Dec. 23, 2017

(51) Int. Cl.
*A01H 5/02* (2018.01)

(52) U.S. Cl.
USPC ..... Plt./356.13

(58) Field of Classification Search
USPC ..... Plt./356.13
See application file for complete search history.

*Primary Examiner* — Annette H Para
(74) *Attorney, Agent, or Firm* — C. A. Whealy

(57) ABSTRACT

A new and distinct cultivar of *Petunia* plant named 'Dopetsmimar', characterized by its compact and mounding to trailing plant habit; moderately vigorous growth habit; freely branching habit; early and freely flowering habit; light red purple and dark red purple bi-colored flowers; and good garden performance.

1 Drawing Sheet

Botanical designation: *Petunia* X *hybrida.*
Cultivar denomination: 'DOPETSMIMAR'.

BACKGROUND OF THE INVENTION

The present invention relates to a new and distinct cultivar of *Petunia* plant, botanically known as *Petunia* X *hybrida* and hereinafter referred to by the name 'Dopetsmimar'.

The new *Petunia* plant is a product of a planned breeding program conducted by the Inventor in Rheinberg, Germany. The objective of the breeding program is to create new compact and early-flowering *Petunia* plants with numerous attractive flowers.

The new *Petunia* plant is a naturally-occurring whole plant mutation of a proprietary selection of *Petunia* X *hybrida* identified as code number TT-0454-X0012, not patented. The new *Petunia* plant was discovered and selected by the Inventor as a single flowering plant from within a population of plants of the parent selection in a controlled greenhouse environment in Rheinberg, Germany in May, 2017.

Asexual reproduction of the new *Petunia* plant by terminal vegetative cuttings in a controlled greenhouse environment in Rheinberg, Germany since June, 2017 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetsmimar'. These characteristics in combination distinguish 'Dopetsmimar' as a new and distinct *Petunia* plant:

1. Compact and mounding to trailing plant habit.

2. Moderately vigorous growth habit.
3. Freely branching habit.
4. Early and freely flowering habit.
5. Light red purple and dark red purple bi-colored flowers.
6. Good garden performance.

Plants of the new *Petunia* can be compared to plants of the parent selection. In side-by-side comparisons, plants of the new *Petunia* differ primarily from plants of the parent selection in the following characteristics:

1. Plants of the new *Petunia* are more compact than plants of the parent selection.
2. Plants of the new *Petunia* have larger flowers than plants of the parent selection.
3. Plants of the new *Petunia* and the parent selection differ in flower color as plants of the parent selection have pink and red bi-colored flowers.

Plants of the new *Petunia* can be compared to plants of *Petunia* X *hybrida* 'Dueswejofa', disclosed in U.S. Plant Pat. No. 26,756. In side-by-side comparisons, plants of the new *Petunia* and 'Dueswejofa' differ primarily in the following characteristics:

1. Plants of the new *Petunia* have thicker lateral branches than plants of 'Dueswejofa'.
2. Plants of the new *Petunia* are more freely flowering than plants of 'Dueswejofa'.
3. Plants of the new *Petunia* have larger flowers than plants of 'Dueswejofa'.
4. Plants of the new *Petunia* and 'Dueswejofa' differ in flower color as plants of 'Dueswejofa' have red purple and dark purple bi-colored flowers.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant.

The photograph is a close-up view of a typical flowering plant of 'Dopetsmimar'.

DETAILED BOTANICAL DESCRIPTION

The aforementioned photographs and following observations, measurements and values describe plants grown during the spring in 22-cm containers in a glass-covered greenhouse in Rheinberg, Germany and under cultural practices typical of commercial *Petunia* production. During the production of the plants, day and night temperatures averaged 18° C. and light levels averaged 4,500 lux. Plants were 13 weeks old when the photograph and description were taken. In the following description, color references are made to The Royal Horticultural Society Colour Chart, 2007 Edition, except where general terms of ordinary dictionary significance are used.

Botanical classification: *Petunia* X *hybrida* 'Dopetsmimar'.

Parentage: Naturally-occurring whole plant mutation of a proprietary selection of *Petunia* X *hybrida* identified as code number TT-0454-X0012, not patented.

Propagation:

- *Type*.—By terminal vegetative cuttings.
- *Time to initiate roots, summer*.—About five days at temperatures about 20° C.
- *Time to initiate roots, winter*.—About seven days at temperatures about 20° C.
- *Time to produce a rooted young plant, summer*.—About three weeks at temperatures about 20° C.
- *Time to produce a rooted young plant, winter*.—About four weeks at temperatures about 20° C.
- *Root description*.—Fine, fibrous; close to 155B in color, actual color of the roots is dependent on substrate composition, water quality, fertilizers, substrate temperature and age of roots.
- *Rooting habit*.—Freely branching; dense.

Plant description:

- *Plant and growth habit*.—Compact, mounding to trailing plant habit; freely branching habit with about four primary lateral branches each with about four to six secondary branches develop after pinching; moderately vigorous growth habit.
- *Plant height, soil level to top of foliar plane*.—About 33 cm.
- *Plant height, soil level to top of floral plane*.—About 34.5 cm.
- *Plant diameter*.—About 92 cm.

Lateral branch description:

- *Length*.—About 82 cm.
- *Diameter*.—About 7.4 mm.
- *Internode length*.—About 3.1 cm.
- *Strength*.—Moderately strong.
- *Aspect*.—Initially upright to outwardly spreading.
- *Texture and luster*.—Pubescent; semi-glossy.
- *Color, developing and fully developed*.—Close to 143C; at the internodes, close to 139D.

Leaf description:

- *Arrangement*.—Before flowering, alternate; after flowering, opposite; simple.
- *Length*.—About 4.6 cm.
- *Width*.—About 2.3 cm.
- *Shape*.—Spatulate.
- *Apex*.—Obtuse.
- *Base*.—Attenuate.
- *Margin*.—Entire.
- *Texture and luster, upper and lower surfaces*.—Pubescent; leathery; semi-glossy.
- *Venation pattern*.—Pinnate; arcuate.
- *Color*.—Developing and fully expanded leaves, upper surface: Close to 137B; venation, close to 137B. Developing and fully expanded leaves, lower surface: Close to 138B; venation, close to 139D.
- *Petioles*.—Length: About 4.5 mm. Diameter: About 2 mm. Strength: Moderately strong. Texture and luster, upper and lower surfaces: Smooth, glabrous; semi-glossy. Color, upper surface: Close to 145B. Color, lower surface: Close to 144C.

Flower description:

- *Flower type and flowering habit*.—Single salverform flowers arising from leaf axils; freely flowering habit with usually about 350 flowers developing per plant during the flowering season; flowers face mostly upright to outwardly.
- *Fragrance*.—None detected.
- *Natural flowering season*.—Plants flower continuously during the spring and summer in Germany; early flowering habit, plants typically beginning flowering about nine weeks after planting.
- *Flower longevity*.—Individual flowers last about two to three days on the plant; flowers persistent.
- *Flower buds*.—Length: About 4.3 cm. Diameter: About 6.5 mm. Shape: Ovoid. Texture and luster: Rippled, glabrous; semi-glossy. Color: Close to 187A.
- *Flower diameter*.—About 5.9 cm.
- *Flower depth (height)*.—About 4.2 cm.
- *Flower throat diameter*.—About 1.3 cm.
- *Flower tube length*.—About 3.2 cm.
- *Flower tube diameter*.—About 2 mm.
- *Corolla*.—Arrangement: Five petals fused at the base and opening into a flared trumpet. Petal lobe length (from throat): About 2.5 cm. Petal lobe width: About 3 cm. Petal shape: Roughly spatulate. Petal apex: Obtuse. Petal margin: Entire; moderately undulate. Petal texture and luster, upper and lower surfaces: Rippled, glabrous; semi-glossy. Throat texture: Rippled, glabrous. Tube texture: Rippled, pubescent. Color: Petal lobe, when opening, upper and lower surfaces: Close to 155C; center, close to 187A. Petal lobe, fully opened, upper surface: Close to 65D; center, close to 72A; venation, close to 202A; color does not fade with development. Petal lobe, fully opened, lower surface: Close to 65D; center, close to 187A; venation, close to 187A; color does not fade with development. Flower throat: Close to 202A; venation, close to 202A. Flower tube: Close to 72B; venation, close to 202A.
- *Calyx*.—Arrangement: Five sepals fused at the base forming a star-shaped calyx. Length: About 2 cm. Diameter: About 3.5 cm. Sepal length: About 2 cm. Sepal width: About 3.1 mm. Sepal shape: Oblong. Sepal apex: Rounded. Sepal margin: Entire. Sepal texture and luster, upper and lower surfaces: Smooth, glabrous; semi-glossy. Color, when opening and fully opened, upper surface: Close to 137A. Color, when opening and fully opened, lower surface: Close to 137C.

*Peduncles*.—Length: About 2.9 cm. Diameter: About 1.1 mm. Strength: Moderately strong. Texture and luster: Smooth, glabrous; semi-glossy. Color: Close to 143C.

*Reproductive organs*.—Stamens: Quantity per flower: Five. Filament length: About 2 cm. Filament color: Close to 145D. Anther length: About 2 mm. Anther shape: Ovate. Anther color: Close to 142D. Pollen amount: Abundant. Pollen color: Close to 128C. Pistils: Quantity per flower: One. Pistil length: About 2.2 cm. Style length: About 2 cm. Style color: Close to 138D and 187A. Stigma diameter: About 2.2 mm. Stigma shape: Rounded. Stigma color: Close to 144A. Ovary color: Close to 141D. Fruits: Length: About 7 mm. Diameter: About 5 mm. Texture: Smooth, glabrous. Color: Close to 11C. Seeds: Quantity per flower: About 80. Length: About 0.8 mm. Diameter: About 0.6 mm. Texture: Smooth, glabrous. Color: Close to 200A.

Garden performance: Plants of the new *Petunia* have been observed to have good garden performance and tolerate wind, rain, temperatures ranging from about 3° C. to about 28° C. and to be suitable for USDA Hardiness Zone 11.

Pathogen & pest resistance: Plants of the new *Petunia* have not been observed to be resistant to pathogens and pests common to *Petunia* plants to date.

It is claimed:

1. A new and distinct *Petunia* plant named 'Dopetsmimar' as illustrated and described.

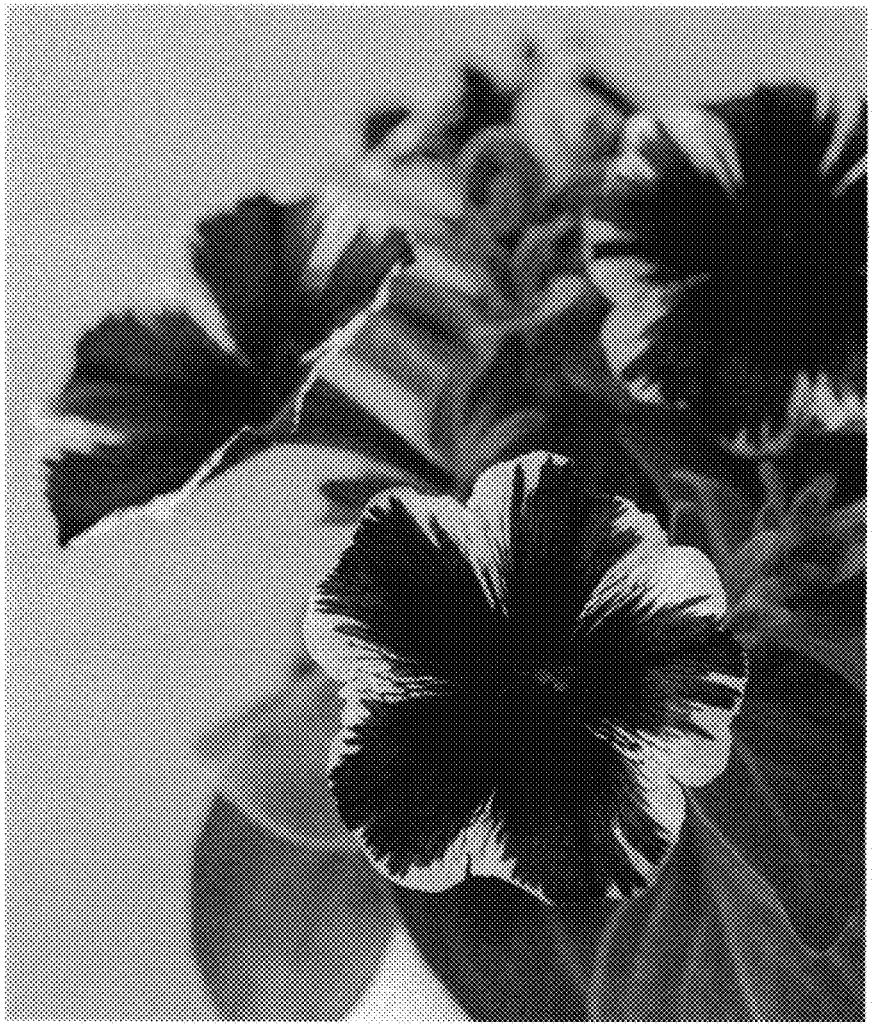

* * * * *